United States Patent [19]

Corr et al.

[11] Patent Number: 5,085,083
[45] Date of Patent: Feb. 4, 1992

[54] FABRICATED PLASTIC TEST SPECIMEN

[76] Inventors: Richard J. Corr; Ann D. Corr, both of P.O. Box 263, Quechee, Vt. 05059

[21] Appl. No.: 566,098

[22] Filed: Aug. 13, 1990

[51] Int. Cl.⁵ ............................................. G01N 3/00
[52] U.S. Cl. ..................................................... 73/760
[58] Field of Search ................. 73/760, 761, 788, 818, 73/819, 821, 822, 826, 827, 834, 835, 839, 841, 842, 843, 844, 845, 849, 847, 848, 850, 852, 853, 851, 865.8, 866

[56] References Cited

U.S. PATENT DOCUMENTS

| | | | |
|---|---|---|---|
| 2,831,344 | 4/1958 | Kaar et al. | 73/851 |
| 4,107,979 | 8/1978 | Saeda et al. | 73/851 |
| 4,358,961 | 11/1982 | Woods, Jr. | 73/827 |

FOREIGN PATENT DOCUMENTS

| | | | |
|---|---|---|---|
| 1260768 | 9/1986 | U.S.S.R. | 73/788 |
| 1265529 | 10/1986 | U.S.S.R. | 73/851 |

*Primary Examiner*—Robert Raevis
*Attorney, Agent, or Firm*—Michael J. Weins

[57] ABSTRACT

This invention relates to a test specimen for generating data to provide a preliminary qualification of plastic materials for fabricated parts without requiring prototype development. The test specimen disclosed has two plates which are designed to be joined in various ways and the resulting joints evaluated. The plates are provided with latches and tabs to test mechanical locking. The test specimens are also provided with a series of grooves, a raised section, posts, holes and self-tapping lugs to allow the samples to be tested for the effectiveness of press fit, heat staking, ultra-sonic welding, adhesive bonding and the effectiveness of self tapping screws. The test specimen can be thermally cycled, held at elevated temperatures and exposed to other environmental conditions to determine the effect of these variables on the performance of the plastic. The effect of various testing conditions on the test specimen can then be assessed with respect to the performance of the bonding and joining techniques used for the test samples. The test specimen can be produced by injection molding in which case gating configuration can be varied to study the effective gating configuration on the properties of the test specimen.

7 Claims, 5 Drawing Sheets

FABRICATED PLASTIC TEST SPECIMEN

FIELD OF INVENTION

This invention relates to a test specimen suitable for evaluating plastics and predicting their fabricated properties by establishing comparative data between the performance of various plastics and attachment means under simulated operating conditions.

BACKGROUND OF THE INVENTION

In selecting plastics for parts it has been the practice to make the selection based on bulk properties or alternatively by testing the performance of a prototype.

Frequently the bulk properties of a plastic do not prove to be the best indicator of how a plastic will perform when used for a part since parts are often made from components which are assembled and held together by various fastening and bonding techniques. In the parts which result the performance is frequently determined by the performance of the fasteners and the bonding between the components.

In other parts a processing step, such as injection molding, can limit the suitability of a plastic for a particular application since the processing steps may introduce distortions in the part.

Still in other situations the part may be successfully molded and assembled, provide adequate strength and dimensional stability, only to deteriorate when exposed to elevated temperatures or to thermal cycling.

Thus there is a need for a test specimen that will provide information of the performance of materials in three dimensional shaped forms and reduce the need to build prototypes for preliminary testing. The test specimen needs to be suitable for testing the performance of plastics as a function of the method of assembly and provide comparative data on the effect of time at temperature and the effect of thermal cycling on the properties of fabricated test specimens.

SUMMARY OF INVENTION

It is an object of the present invention to provide a two part test specimen which can be assembled, joined, mechanically locked, and bonded in various ways and tested.

It is another object of the invention to provide a test specimen that can be thermally cycled to test the effect of thermal cycling on the performance of bonded joints, fasteners, and mechanical locking of the parts.

It is still a further object to provide an injection molded test specimen where alternate gate configurations are employed to provide information on the effect of the gate placement on shape distortion and dimensional stability.

It is another object of the invention to determine the effect of gate placement on the thermal and mechanical properties of a resulting part.

These and other objects of the invention will become apparent to one skilled in the art from the following description, figures, and claims.

The test specimen of the present invention is a two part specimen provided with multiple means for joining and fastening the parts. The test specimen is designed to allow a selected combination of joining and fastening means to be tested and to allow evaluation of their performance.

The test specimens are injection molded and are provided with two alternate gating configurations, a central gate and an end gate. These gate configurations offer two extremes in gate placement and provide comparative data on the effect of end gating and central gating on the resulting properties of the test specimen.

In addition to comparative tests between various materials and attachment means, the test specimen can be used to provide information on the creep of thermal cycling on the properties of the test specimen.

The test specimen in its simplest form has two plates. The first plate has a closed wall attached thereto. The closed wall has a first edge which attaches to the plate forming an open compartment which is an integral part of the first plate. A second edge of the closed wall is a free edge and serves as a rim of the compartment. The rim is provided with a groove creating a stepped rim. It is preferred that this compartment be rectangular in cross section.

The first plate is preferably thicker than the second plate. Having a thick plate increases the volume which reduces the problems associated with gating. A thick plate also provides heavier sections where the shrinkage patterns will be more apparent.

The second plate has on its first side a raised section which is contoured to engage the groove in the rim of the compartment. These engaging surfaces provide mating surfaces for establishing an adhesive bond between the first plate and the rim of the compartment. Typically, epoxy glues or solvents can be employed as the adhesive bonding agent.

The second plate has a set of ultra-sonic welding ridges on its second side. The ridges are configured to engage the grooves in the rim of the compartment formed on the first plate. The set of ultra-sonic welding ridges have heights suitable for ultra-sonic welding. Typically the height of the ultra-sonic welding ridges will be about 10% higher than the depth of the groove in the rim. When the ridges are ultra-sonically welded to the groove in the rim of the wall of the compartment of the first plate, data on weld performance can be generated.

Posts are attached to one of the plates and post holes which align with the posts are provided to the other plate.

Preferably the posts are attached to the first side of the first plate. Post holes are positioned on the second plate such that the posts pass through the post holes. It is further preferred that the post and post holes be so configured that the combination can be employed to test for press fits as well as for thermal staking. In order that the post and post hole combination can serve these two functions, it is further preferred that the post have a base section and a top section with the base section having a diameter greater than the diameter of the top section creating a dual section post.

The holes which are employed with the dual section posts are passages having a first passage section and a second passage section. The first passage section has a diameter so that when it engages the first section of the stake a press fit will result. The second section has a larger diameter and its engagement with the first section of the post will not result in a press fit. In order to provide sufficient length for the passages it is preferred that bosses are provided on the second side of the second plate. The bosses contain the first section of the passage and the passages extends for a length sufficient to provide sufficient frictional contact between the first post section and the first passage section to provide a press fit. Typically press fits are maintained providing a negative clearance of 0.001 in. per in. of diameter and a length of contact parallel to the axis of the post will be about equal to the diameter of the hole.

For the post and post holes having the preferred configuration discussed above the performance of the press fit can be made by assembling the first plate and the second plate such that the second side of the second plate engages the rim of the compartment of the first plate. This will place the press fit section of the post, the first section of the post, in contact with the first section of the passages.

It is preferred that the posts are positioned in the open compartment and that the compartment be rectangular in shape. This configuration provides a test sample with a rectangular cross section which can be tested with standard testing equipment.

The smaller diameter section of the posts serve as heat stakes. In order to evaluate the performance of the heat stakes for the preferred stake hole configuration, the first and second plate are assembled such that the first side of the second plate engages the rim of the compartment of the first plate. With the stakes so positioned there will be clearance between the stakes and the passage sections. The heat stakes are heated and pressure is applied to create a flared segment of the stake "rivet type structure" which overlaps the region of the plate around the post holes through which the stakes pass.

Lugs are provided which are preferably located on the first plate. Screw holes are provided which align with the lugs and are located on the opposite plate. When the lugs are located on the first plate, the preferred location, the screw holes will be on the second plate. The lug and screw combination allows testing the attachment of the plates when fastened by self tapping screws. Again, it is preferred that the lugs be located within the open rectangular compartment for the reasons set forth above with regard to the posts. Having the depth of the compartment about ¼ in. provides sufficient depth to allow lugs to be contained therein and provides sufficient height to assure sufficient engagement of the threads of a standard self tap screw such as a #4-40 screw.

Locking latch - tab combinations provide another means for attaching the two plates. Preferably the latches are attached to the first side of the second plate. The latches are positioned such that they will engage the tabs on the opposite plate. It is further preferred that the latch is an "L" shaped protrusion with the longer leg substantially normal to the second plate while the shorter is parallel to the second plate. Having the latches attached to the second plate, which is the thinner of the plates, and attaching the longer leg to the second plate provides increased mobility of the latches, making it easier to engage and disengage of the latches with the tabs.

The plastics suitable for testing with the test specimen can vary in stiffness, so to accommodate the stiffer plastics it is desirable to provide additional flexibility to the latches. Preferably this can be accomplished by providing paired cutouts and depressions in the plate adjacent to the latches. The cutouts are provided beside the attached legs of the latches and under the projection of the unattached leg of the latches. The depressions in the plate are located next to the attached legs on the side opposite the cutouts. These paired cutouts and depressions facilitate the latches swinging away from the tabs into which the latches engage.

THE BEST MODE OF CARRYING THE INVENTION INTO PRACTICE

Figure 1:
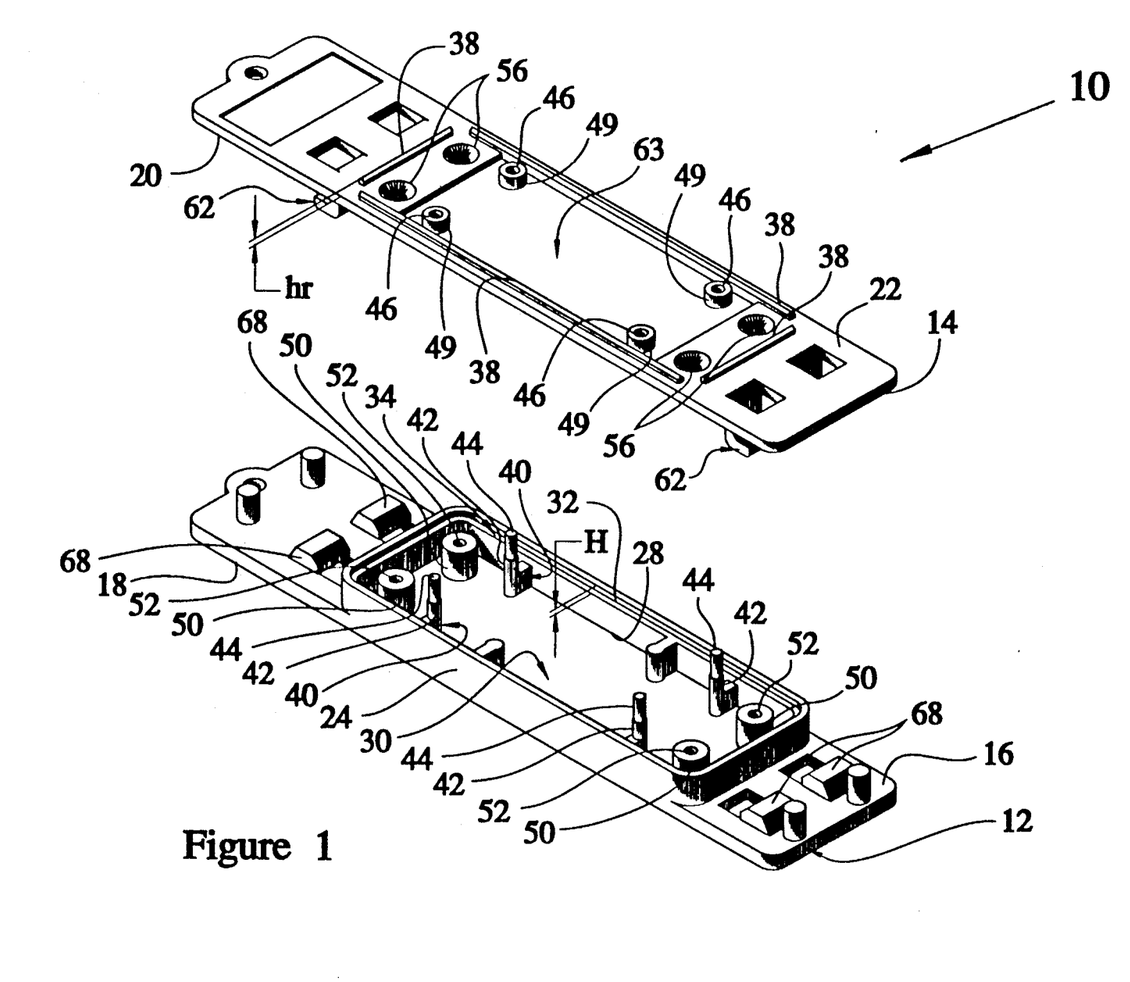
FIG. 1 is an exploded view of one embodiment of a two part test sample of the present invention showing a perspective view of the second side of the second plate. As illustrated, the latches will engage the tabs when the parts are assembled.

FIG. 1 is an exploded view of a test specimen 10. The test specimen 10 has a first plate 12 and a second plate 14. The first plate 12 has a first side 16 and a second side 18. The second plate 14 has a first side 20 and a second side 22. The first plate 12 has a closed wall 24 having an upper edge 26 and a lower edge 28. The lower edge 28 attaches to the first side 16 of the first plate 12 forming in combination with the plate 12 an open compartment 30. A groove 32 having a depth H is provided in the upper edge 26 of the closed wall 24 forming a stepped rim 34.

Figure 2:
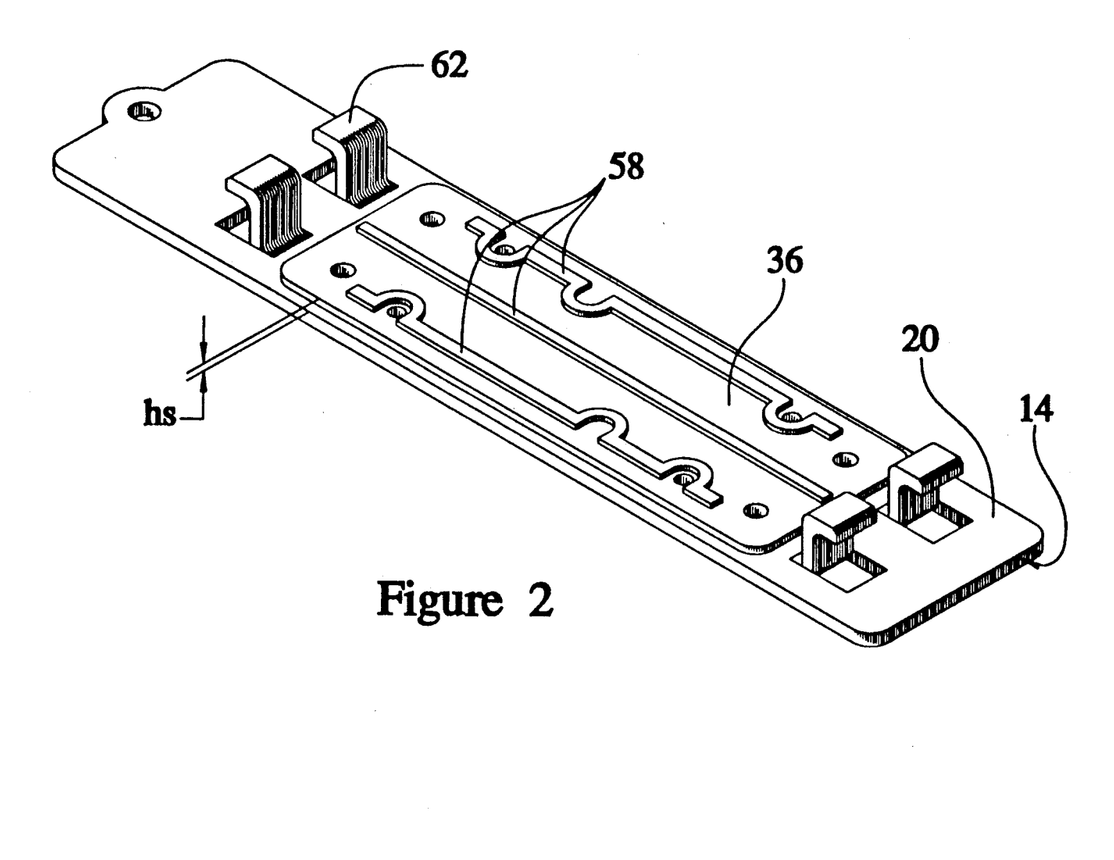
FIG. 2 is a view of the test sample of FIG. 1 showing a perspective view of the first side of the second plate.

FIG. 2 illustrates the first side 20 of the second plate 14. A raised section 36 is formed on the first side 20 of the second plate 14. The height $h_s$ of the raised section is preferably the same as the depth H of the groove 32. The raised section 36 and the groove 32 and the rim 34 of the closed wall section 24 are so proportioned that the raised section 36 slidably engages the groove 32 of the rim 34 of the open compartment 30. (Shown in FIG. 1)

When the first plate 12 and the second plate 14 are assembled so that the first sides 16 and 20 of each of the two plates 12 and 14 face each other, the two plates 12 and 14 can be connected by bonding the groove 32 and the raised section 36. Epoxy, glues or solvents can be used to bond the two parts together.

The second side 22 of the second plate 14 shown in FIG. 1 has ultra-sonic welding ridges 38 which are positioned to engage the groove 32. The height $h_r$ of the ridges 38 being greater than the depth H of the groove 32. These ridges 38 provide an additional means for attaching the first plate 12 to the second plate 14.

When the first plate 12 and the second plate 14 are positioned such that the ultra-sonic welding ridges 38 engage the groove 32, a gap resulting from the additional height of the ridges 38 is reduced by ultra-sonic welding of the ridge 38 to the groove 32.

In other words when the second side 22 of the second plate 14 faces the first side 16 of the first plate 12, the ridges can be ultra-sonically welded to the groove 32 to bond the first plate 12 to the second plate 14.

In order that the ultra-sonic welding will be strong, it is preferred that the ridges have a height $h_r$ of 10% greater than the height H of the groove 32.

In the embodiment of FIG. 1, posts 40 having a first section 42 and a second section 44 are attached to the first side 16 of the first plate 12. The first section 42 has a diameter greater than the second section 44. Posts 40 are so positioned to engage post holes 46 which pass through the second plate 14.

Figure 3:
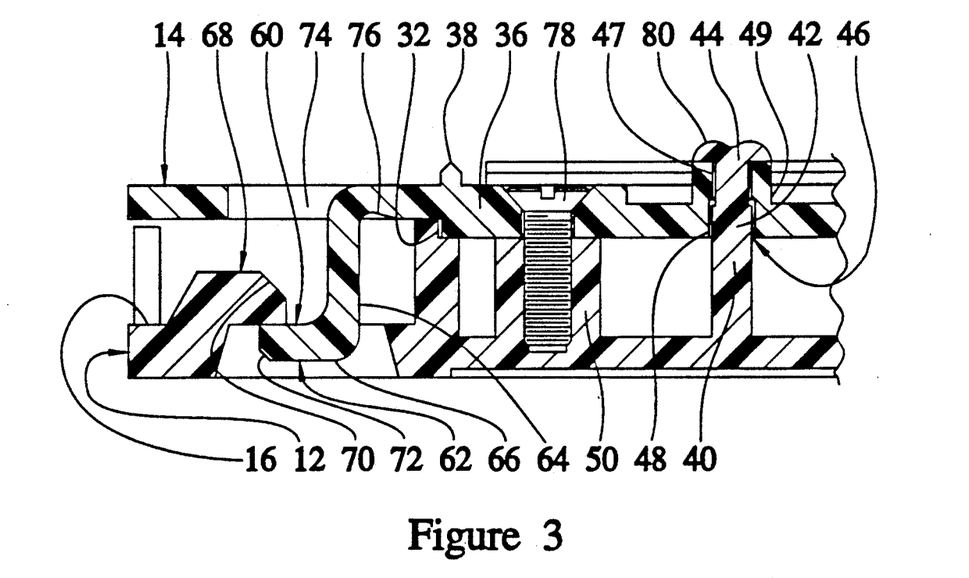
FIG. 3 is a cross section of an assembled section of the test specimen as illustrated in FIG. 1 illustrating the various attachment means.
Figure 4:
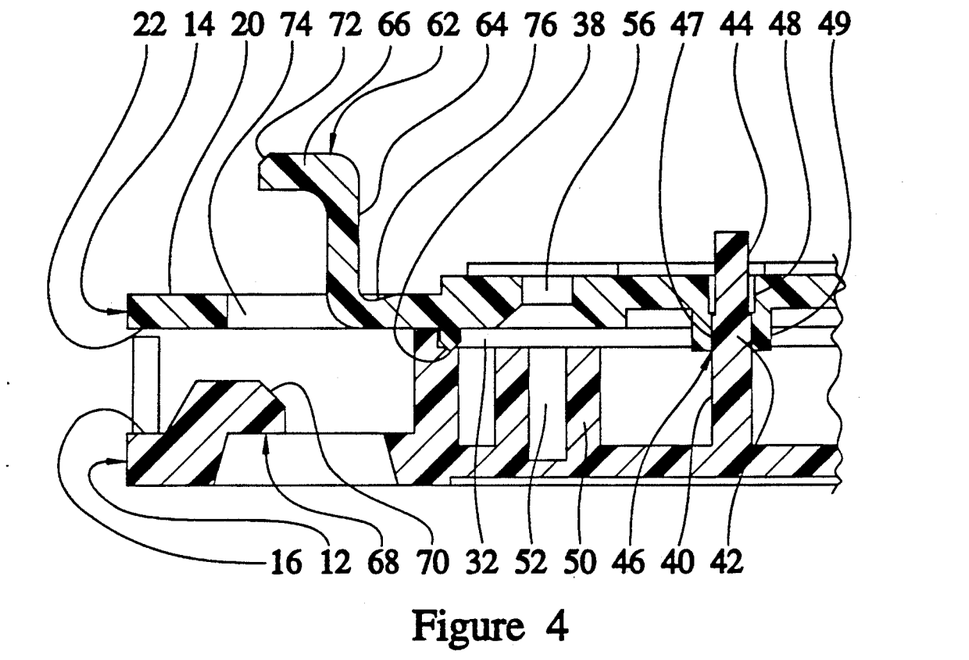
FIG. 4 is a cross section of an assembled section of the test specimen with the latches not engaging.

The post hole 46 shown in cross section in FIG. 3 and 4 have a first post hole section 47 forming a passage having a diameter that will provide a press fit with the first section 42 of the post 40. Typically, a negative clearance of 0.001 in. per in. of diameter is employed and the length of contact region should be approximately that of the diameter of the passage. The post holes 46 have a second section 48 forming a passage with a larger diameter and when positioned around the post will not produce a press fit. Preferably, bosses 49 shown in FIG. 1 are provided to extend the length of the passages and are positioned on the second side 22 of the plate 14.

Placement of the post 40 on the first plate 12 provides additional rigidity to the post 40 since the first plate 12 is preferably thicker than the second plate 14 and the first plate 12 is stiffened by the closed wall 24.

Lugs 50 are preferably provided on the first side 16 of the first plate 12. These lugs 50 have holes 52 for self tapping screws (shown in FIG. 3). The holes 52 in the lugs 50 have a diameter which matches the root diameter of the self tapping screw. On the second plate 14 aligning with the lugs 50 on the first plate 12 are screw holes 56. Preferably the screw holes 56 are counter-sunk so the screws when set will be flush with the second side 22 of the second plate 14.

Latches 62 are preferably attached to the first side 20 of the second plate 14, these latches 62 engage tabs 68 on the first side 16 of the first plate 12. Having the first plate 12 thicker than the second plate 14 provides flexibility in the second plate 14 which assists in latching and unlatching the second plate 14 to the first plate 12.

It is preferred that the second plate 14 have a recess 63 in the second side 22 of the second plate 14 which is opposite the raised section 36 on the first side 20 of the second plate 14. This reduces the variation in thickness of the second plate 14. It is further preferred for additional rigidity that stiffening ribs 58 shown in FIG. 2 be attached to the raised section 36 of the first side 20 of the second plate 14.

FIG. 3 shows in cross section an assembled specimen with the first side 16 of the first plate 12 facing the first side 20 of the second plate 14. This figure does not include the optional stiffening ribs 58. FIG. 3 illustrates the operation of various bond, fastening and locking mechanisms provided by the present invention.

The specimen assembled as shown in FIG. 3 illustrates details of the locking latch-tab assembly 60. The latches 62 are "L" shaped having the longer legs 64 attached to the first side 20 of the second plate 14 while the shorter legs 66 are substantially parallel to the second plate 14. The shorter legs 66 engage the tabs 68. Having the latches 62 configured with a long and short leg and having the long leg 64 mounted to the second plate 14 increases the flexibility of the latches 62. The latches 62 engage the tabs 68 in a snapable manner allowing engagement and disengagement of the latches 62. The tabs 68 are provided with a beveled tab edge 70 and a beveled leg edge 72 is provided to the shorter legs 66. The bevels are so positioned that they will slide by each other when pressure is applied to engage the latches 62 with the tabs 68. In order to increase the flexibility in the latches 62, it is further preferred that paired cutouts 74 and depressions 76 be provided in the second plate 14 adjacent to the latches 62. The cutouts 74 are provided adjacent to the longer leg 64 which attaches to the second plate 14 and are positioned below the the projection of the shorter leg 66 of the latch 62. The depressions 76 in the second plate 14 are positioned adjacent to the opposing side of the longer leg 64.

The test specimen, as shown in FIG. 3, illustrates the use of multiple fastening and bonding means. In addition to the first plate 12 being fastened to the second plate 14 by the latch - tab assembly 60, the plates are secured by bonding the groove 32 to the raised section 36. Self tapping screws 78 are also employed which engage the lugs 50. Finally posts 40 are heat sealed providing deformed head 80 creating a rivet-type coupling.

FIG. 3 also shows details of the bosses 49 which attach to the second side of the second plate 14 and the post holes 46. The post holes 46 are made of a first passage section 47 which has a diameter such as to create a press fit with the first sections 42 of the posts 40. The second section 48 has a diameter greater than that of the first section 47. Since the second section 44 of the post 40 has a smaller diameter than the first section 42 there will be clearance between the hole 46 and the post 40 as illustrated in FIG. 3 when the first side 20 of the second plate 14 faces the first side 16 of the first plate 12. Thus, heat sealing the post 40 will provide a true test of the thermal stake bond strength.

While the assembled specimen of FIG. 3 is shown with multiple attachment means employed, one may, if desired, selectively use any limited combination of attachment means provided. For example, the latches 62 could be removed, the screws 78 not employed and the stakes 40 removed, leaving only the bonding between the groove 32 and the raised section 36.

FIG. 4 shows the test specimen assembled with the second side 22 of the second plate 14 facing the first side 16 of the first plate 12. Again, as with FIG. 3, the stiffening ribs 58 have not been shown.

When so positioned, the ultra-sonic welding ridges 38 engage the groove 32 leaving a slight gap between the second surface 22 of the second plate 14 and the rim 34. Ultra-sonic welding of the ridges 38 to the grooves 32 deforms the ultra-sonic welding ridges 38 reducing the gap between the rim 34 and the second side 22 of the second plate 14. As illustrated in FIG. 4 there is also a press fit between the first section 42 of the post 40 and the first section 47 of the post holes 42. The first section 40 of the passage 46 provides a press fit with the first section 42 of the post 40. For a press fit it is standard practice that the diameter of the first section 47 of the passage 46 should provide a negative clearance of typically 0.001 in/in of diameter and the length of the contact region should be approximately that of the diameter of the first section 47 of the passage 46.

Figures 5, 6:
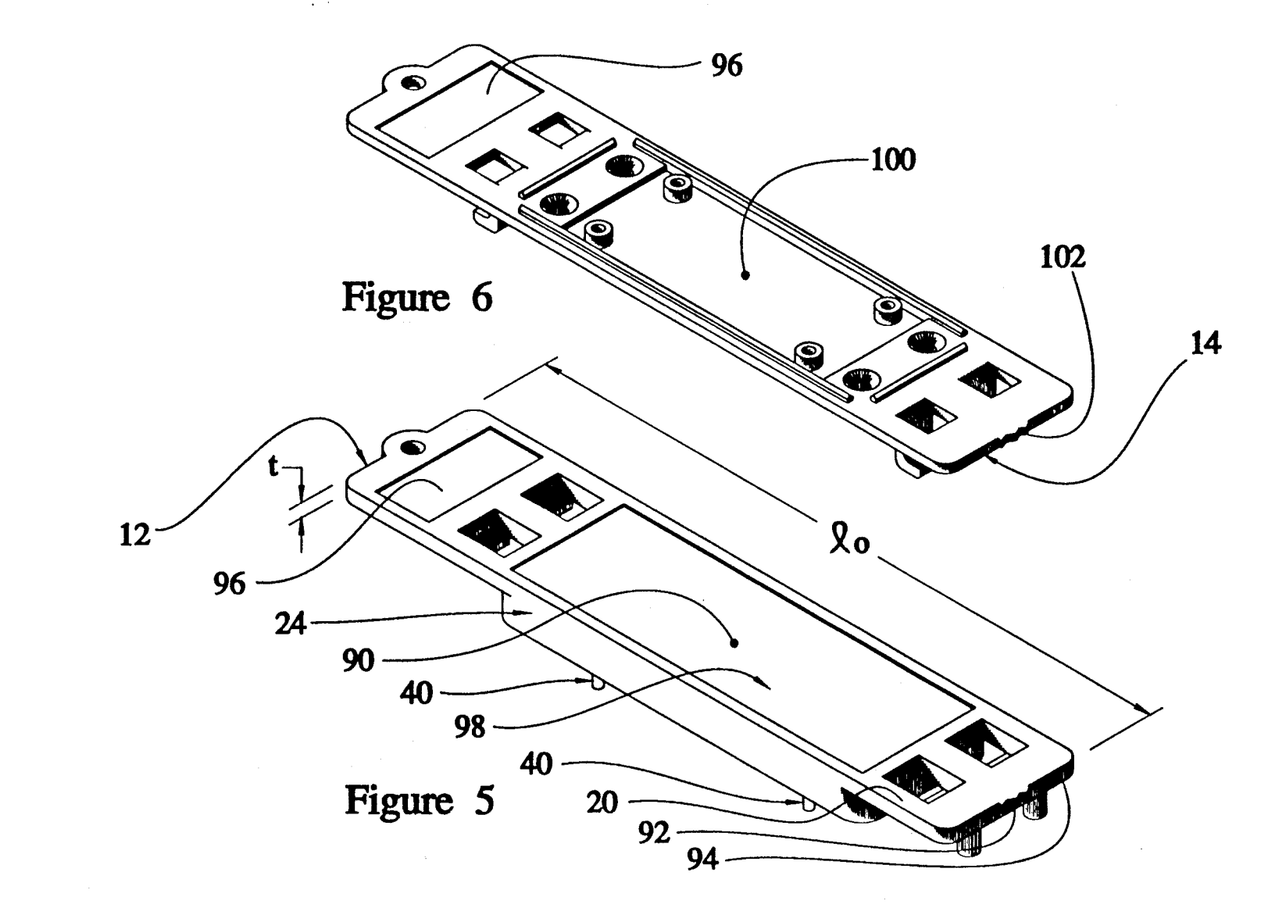
FIG. 5 illustrates two alternate gating systems for the first plate of the present invention shown in FIG. 1.
FIG. 6 illustrates two alternate gating systems for the second plate of the present invention shown in FIG. 1.

FIG. 5 illustrates two alternate gates for filling an injection mold used to form the first plate 12. Both gates are connected to the plate 12. The first plate 12 with additional elements extending therefrom such as the closed wall 24, the post 40 and lugs 44 (not shown in FIG. 5) produce a complex shape which is representative of a typical injected mold part. The first plate 12 with extensions has a region with a varied cross section and a variety of holes and protrusions which provides a mold cavity of intermediate complexity.

It is preferred that the first plate 12 have a thickness t of 2-5% of the overall length 1 of the part to provide adequate mold filling capacity by injection molding.

A central gate 90 is located on the second side 20 of the first plate 12. This central gate 90 is preferred for injection molding since it provides for better distribution of the plastic through the mold and will minimize distortion providing more uniform properties.

Alternatively an end gate 92 can be employed to feed the first plate 12. The end gate 92 attaches to the first plate 12 in the center of one end 94 of the plate 12. The end gate 92 feeds from the second side 20 of the plate 12. This flow pattern will result in more directional properties. However, so gated it should produce a fully formed part if the plate thickness of about one eighth inch or greater is employed. The depression 96 is provided for insertion of information such as material identification. This is done with a die set. A shallow depression 98 is also provided in the central area of the second surface 20 of the first plate 12. Into this depression 98 can be placed letters or other shapes. The ability to fully form such letters or shapes provides an index as to the difficulty to fill the top surface of the pattern. The depression 98 can also be used to inscribe a logo or trademark.

FIG. 6 illustrates two alternate gates for filling an injection mold used to form the second plate 14. The second plate 14 provides a more regular cross section than the first plate 12. This more regular cross section will be easier to fill than the configuration associated with the first plate 12. It is preferred that the second plate 14 be about ⅔ of the thickness of the first plate 12. This will provide adequate thickness to feed the mold and provide a fully formed part. The plate preferably has a depression 96 as is provided in the first plate 12 for insertion of information such as the material identification.

Again a central gate 100 and an end gate 102 are provided for filling an injection mold in which the second plate 12 is formed. The second plate 14 provides an additional index to the performance of a particular plastic for different mold conditions.

Figure 7:
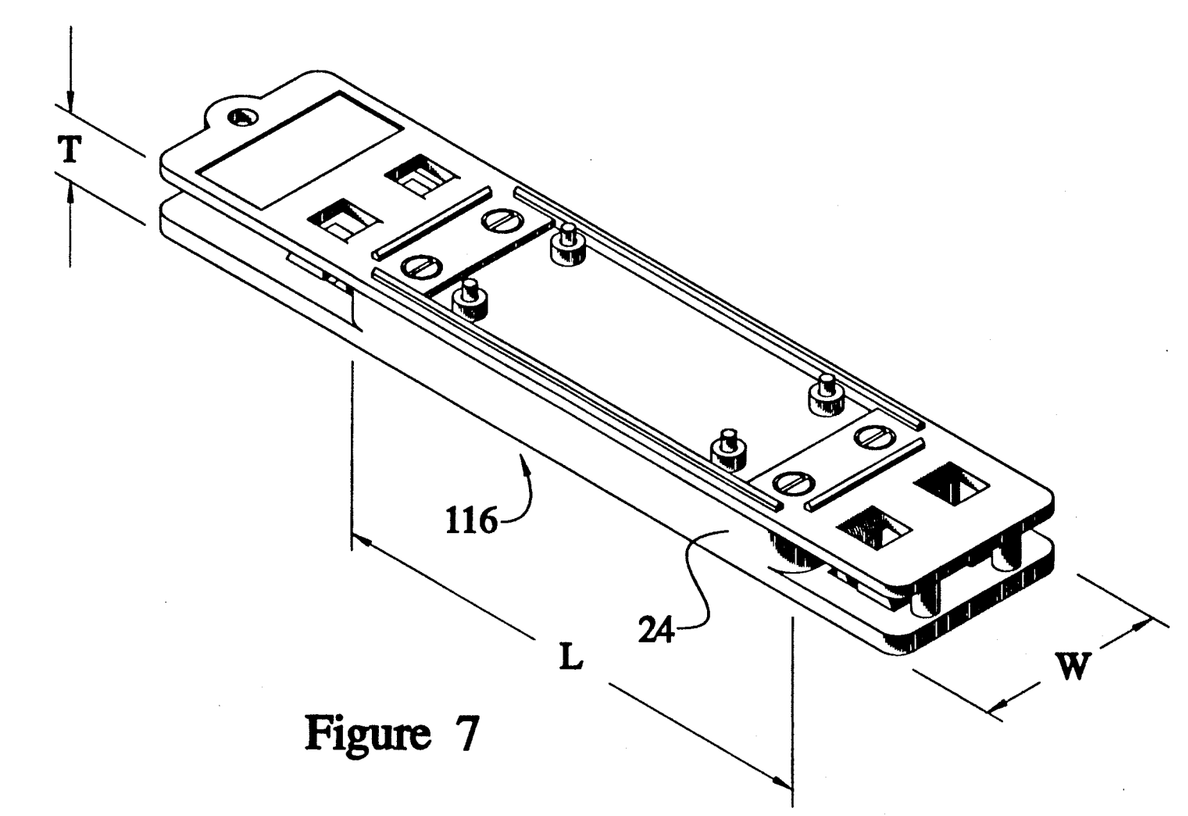
FIG. 7 shows an assembled test sample.

FIG. 7 shows an assembled test specimen of a preferred geometry. The test specimen, as shown, has an effective volume formed by sections bounded by the closed wall 24 creating a rectangular volume 116 having for its length (L), its thickness (T) and its width (W). This effective volume 116 forms a uniform-shaped specimen suitable for conventional testing such as three-point bending, impact tests and tensile testing.

The test specimens provide a means for conducting comparative studies and making preliminary selections of the appropriate materials for a particular application without requiring actual prototypes to be built.

In order to employ the sample for comparative studies one selects the materials of interest and has them injected molded to the shape of the test specimen.

Each of the samples is assembled using one or more bonding or fastening means from the group of: adhesive bonding, ultra-sonic welding, press fit, heat staking, self tapping screws, and a latch-tab locking system.

The samples are tested under conditions which would simulate the proposed use of the parts to be made from the material. A typical test would include creep test, rupture test, thermal cycling of the sample, and environmental exposure. The samples are then observed and the results for the different materials are compared.

Once a material is selected a series of tests on a particular material can be conducted to evaluate the effectiveness of various bonding and fastening techniques for a particular material.

While the present invention has been described in terms of specific embodiments and particular examples, it is appreciated that certain substitutions can be made by those skilled in the art without departing from the spirit of the invention.

What I claim is:

1. A test specimen for comparing properties of plastics as they will perform in fabricated parts comprising:
   a first plate having a first side and a second side;
   a second plate having a first side and a second side, said second plate being attachable to said first plate;
   a closed wall having an upper edge and a lower edge, said lower edge being attached to said first plate forming an open compartment with said first plate, and said upper edge forming a rim of said open compartment;
   a groove in said rim creating a stepped rim;
   a raised section on said first side of said second plate, said raised section being configured to slidably engage said groove in said rim;
   ridges for ultra-sonic welding, said ridges configured to engage said groove in said rim of said compartment, said ridges being positioned on said second surface of said second plate;
   posts attached to one of said plates;
   post holes positioned in said other plate to engage said posts;
   lugs attached to one of said plates for tapping with self threading screws;
   screw holes positioned to align with said lugs in said other plate;
   latches attaching to one of said plates; and
   tabs provided on said other plate to engage said latches,
   whereby the properties of plastics as they will perform in fabricated parts can be compared.

2. The test specimen of claim 1 wherein said posts are attached to said first plate with said post holes passing through said second plate;
   said lugs are attached to said first surface of said first plate with said screw holes passing through said second plate; and
   said latches are on said second plate with said tab on said first plate.

3. The test specimen of claim 2 wherein said posts have a first section and a second section;
   said first section being closer to said first plate and said post holes having a first passage section and a second passage section;
   further comprising bosses on said second side of said second plate;
   said bosses containing said first passage section of passage forming a press fit with said first section of said post, while said second passage section having a larger diameter.

4. The test specimen of claim 3 wherein said latches are "L" shaped having a short leg and a long leg, said long leg being attached to said second plate.

5. The test specimen of claim 4 further comprising:
   cutouts in said second plate adjacent to said long leg of said latch and positioned below the projection of said short leg; and depressions in said second plate, said depressions adjacent to said long leg of said latch and opposite said cutouts.

6. The test specimen of claim 4 wherein said posts and said lugs are positioned in said compartment.

7. The test specimen of claim 6 further comprising:
stiffening ribs attached to said raised section of said first side of said second plate; and
a recess in said second side of said second plate which substantially aligns with said raised section.

* * * * *